United States Patent
Bühler

(10) Patent No.: US 6,702,816 B2
(45) Date of Patent: Mar. 9, 2004

(54) FEMUR MARROW NAIL FOR INSERTION AT THE KNEE JOINT

(75) Inventor: Daniel W. Bühler, Wallisellen (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 10/140,898

(22) Filed: May 7, 2002

(65) Prior Publication Data

US 2002/0183750 A1 Dec. 5, 2002

(30) Foreign Application Priority Data

May 25, 2001 (EP) .............................. 01810517

(51) Int. Cl.$^7$ .............................. A61B 17/72
(52) U.S. Cl. .............................. 606/62
(58) Field of Search .............................. 606/60, 62, 64–67

(56) References Cited

U.S. PATENT DOCUMENTS

| | | | |
|---|---|---|---|
| 5,472,444 A | 12/1995 | Huebner et al. | |
| 5,480,402 A | 1/1996 | Kim | |
| 5,779,705 A | 7/1998 | Matthews | |
| 6,296,645 B1 | * 10/2001 | Hover et al. | 606/62 |

FOREIGN PATENT DOCUMENTS

| | | |
|---|---|---|
| EP | 0 355 411 A1 | 2/1990 |
| EP | 0 827 717 A2 | 3/1998 |
| EP | 0 853 923 A1 | 7/1998 |
| EP | 1 095 626 A1 | 5/2001 |
| FR | 2 718 013 A1 | 10/1995 |

OTHER PUBLICATIONS

M.E. Muller et al., "Manual der Osteosynthese" Springer–Verlag Berlin Heidelberg 1992 (4 pages).*

* cited by examiner

*Primary Examiner*—Kevin Shaver
*Assistant Examiner*—Michael B. Priddy
(74) *Attorney, Agent, or Firm*—Christie, Parker & Hale, LLP

(57) ABSTRACT

The invention describes a femur marrow nail for insertion between the condylii of a knee joint having an anchoring (4) in the region of the nail tip (3), having a curvature (6) extending in the sagittal plane (5) and having a straight end piece (7) which has fastening bores (12, 13) with axes B, C for its fastening. At least two fastening bores (12, 13) with axes B and C cross the longitudinal axis X of the end piece (7) at a spacing $X_2$, $X_3$ less than 70 millimeters from the end (8) of the end piece (7), and with their axes B and C penetrating a plane (10) which includes the end (8) and is perpendicular to the longitudinal axis X at a distance r from the X axis in a region of 10 mm$\leq$r$\leq$116 mm in order to grip hard bone zones with fastening screws (15, 16) in the region of the condylii.

11 Claims, 5 Drawing Sheets

FEMUR MARROW NAIL FOR INSERTION AT THE KNEE JOINT

CROSS REFERENCE TO RELATED APPLICATION

Figure 1:
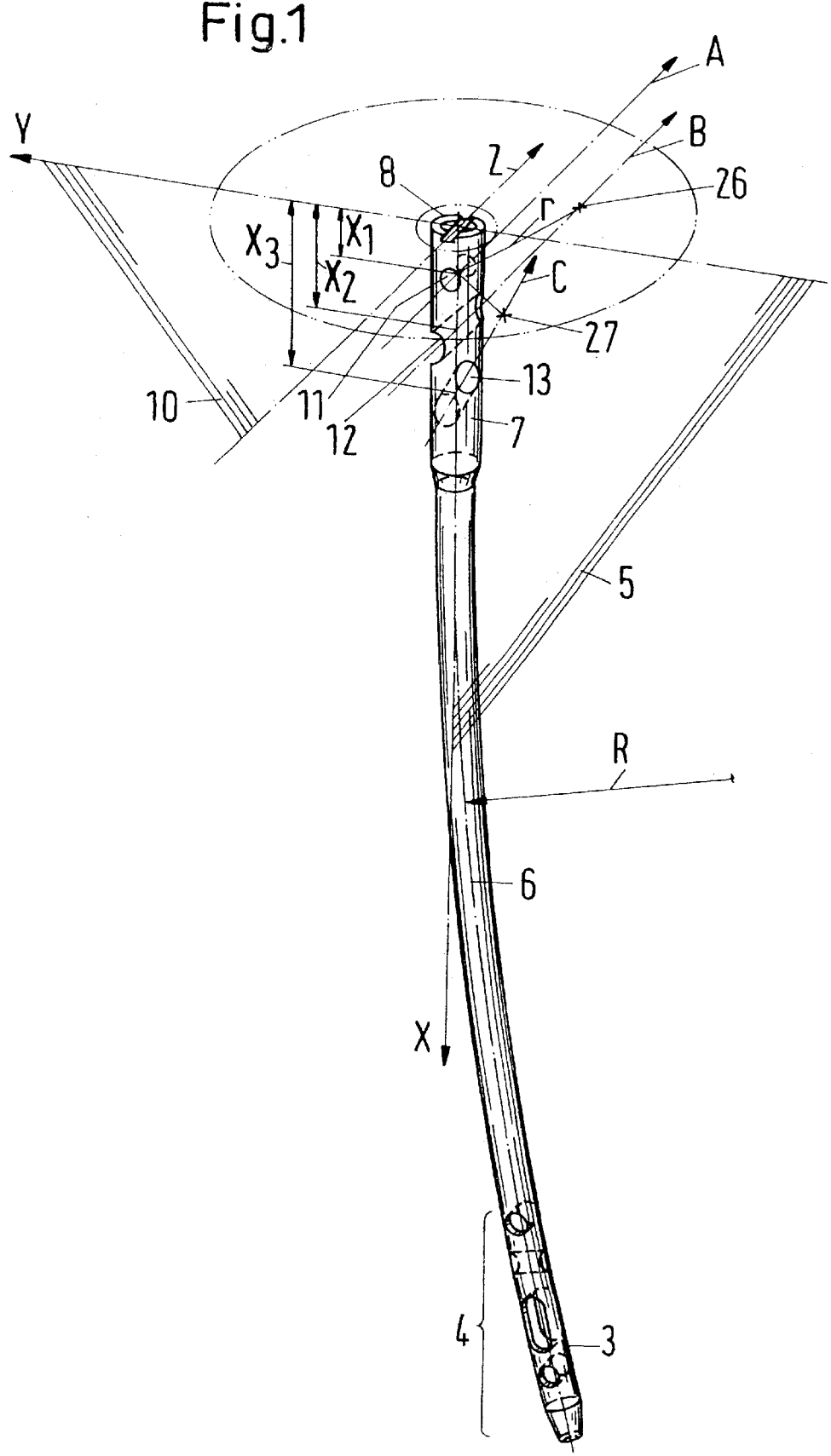

This application claims priority of European Patent Application No. 01810517.1, filed May 25, 2001.

The invention relates to a femur marrow nail for insertion between the condylii of a knee joint having an anchoring in the region of the nail tip, having a curvature provided in the sagittal plane and having a straight end piece which has fastening bores with axes B, C for its fastening.

Such femur marrow nails are used when an opening occurs in the knee joint. It frequently occurs in accidents that fragments are produced in the region of the condylii of the knee joint. The previous healing methods consist of plates attached to the femur bone with bone screws (Manual of osteosynthesis, Springer Verlag, 1992: FIGS. 12.10; 12.11; 12.12), which result in a large operation field or in marrow nails such as are shown in patent application EP-A-0 827 717.

In EP-A-0 827 717, a plurality of screw connections extending parallel to one another through a shank are shown, with their entrance apertures, and possibly their exit apertures, lying in the region of the actual joint and being able to have effects on ligaments, nerves and blood vessels and thus indirectly making the healing process more difficult. The invention is intended to counter this circumstance. It has the object of improving the fixing of fragments in the condylar region and achieves this by at least two fastening bores with axes B and C crossing the longitudinal axis X of the end piece at a spacing of less than 70 millimeters from the end of the end piece and penetrating with its axes B and C a plane which includes the end and is perpendicular to the longitudinal axis X at a spacing r from the X axis in a region 10 mm$\leq$r$\leq$116 mm in order to grip hard bone zones with fastening screws in the region of the condylii.

This arrangement has the advantage that an anchoring can be effected in the spreading direction and in hard bone layers, for example in posterior regions of the condylii, in the condylii which are spread apart from the longitudinal axis of the femur bone like the upper part of a "Y". A further advantage lies in the fact that only a minimum of bone openings is required in the direct region of the joint surfaces.

Advantageous further developments of the invention result from the dependent claims 2 to 12. The following number data for angles relate to a right knee. The system must be imagined in a mirror image for a left knee.

Particularly favourable arrangements result when, in a projection in the direction of the longitudinal axis X of the end piece, the axis B extends in an angle region of $35°\leq\beta_2\leq55°$, and the axis C in an angle region $30°\leq\beta_3\leq45°$, to the sagittal plane and when the axis B forms an angle of $110°\leq\alpha_2\leq150°$, and the axis C an angle of $125°\leq\alpha_3\leq160°$, with the longitudinal axis X. The associated bone screws can be inserted particularly far into the condylii in such an arrangement and support these without the joint surfaces and their direct environment being impaired.

If the longitudinal axis X is crossed perpendicular to the sagittal plane, when considered from the end of the marrow nail, by an axis A of a transverse verse bore at a spacing of 10 mm$\leq X_1 \leq$18 mm, by the axis B at a spacing of 20 mm$\leq X_2 \leq$42 mm, and by the axis C at a spacing of 30 mm$\leq X_3 \leq$70 mm, the hard posterior bone regions can be reached for different condylus sizes.

A better guide length can be achieved for the bone screw with an end piece whose diameter is greater than that of the remaining marrow nail. At the same time, a larger radial support surface is produced for the end piece in the bone. The finding of the bores in the axes A, B and C is carried out by a target wire which is fastened in form-locking manner to the driven in marrow nail and which has bore guides in the direction of the axes A, B and C in order to bore the bone up to the bores in the marrow nail with a smaller diameter than that of the later bone screws. The bone screws can be self-tapping.

The marrow nail can be provided with a kink between the end piece and the actually longer part of the marrow nail. Such a kink allows the end piece to be made straight and within low tolerances in the region of the target wire and nevertheless to follow the curvature of the femur bone in the sagittal plane. The kink is kept smaller than 8° in order to remain in the region of the curvature of the femur.

In accordance with a usual operation technique, the bone marrow can be hollow, that is cannulated, in order to be driven in along a guide wire. It can also have an elongate slit outside the end piece in order to achieve a greater elasticity.

Figure 2:
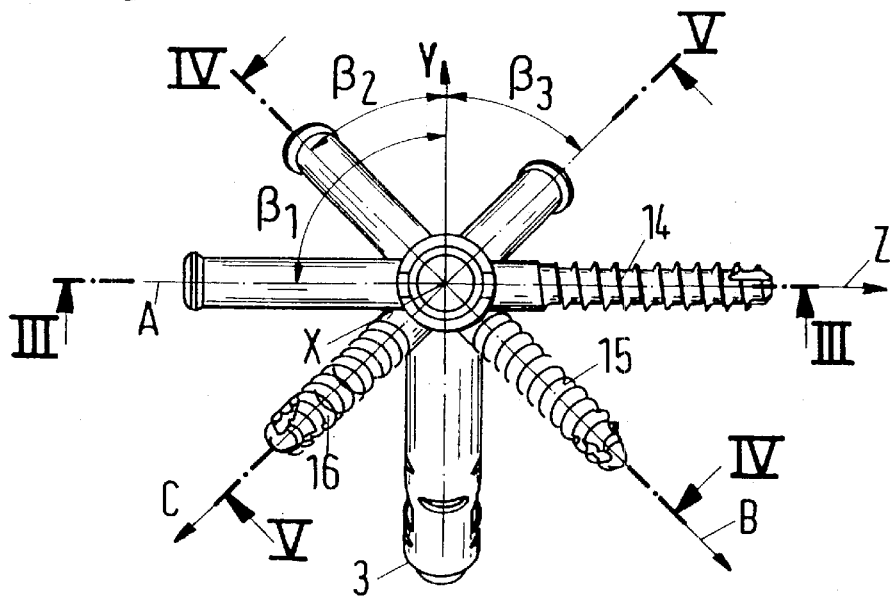
Figure 3:
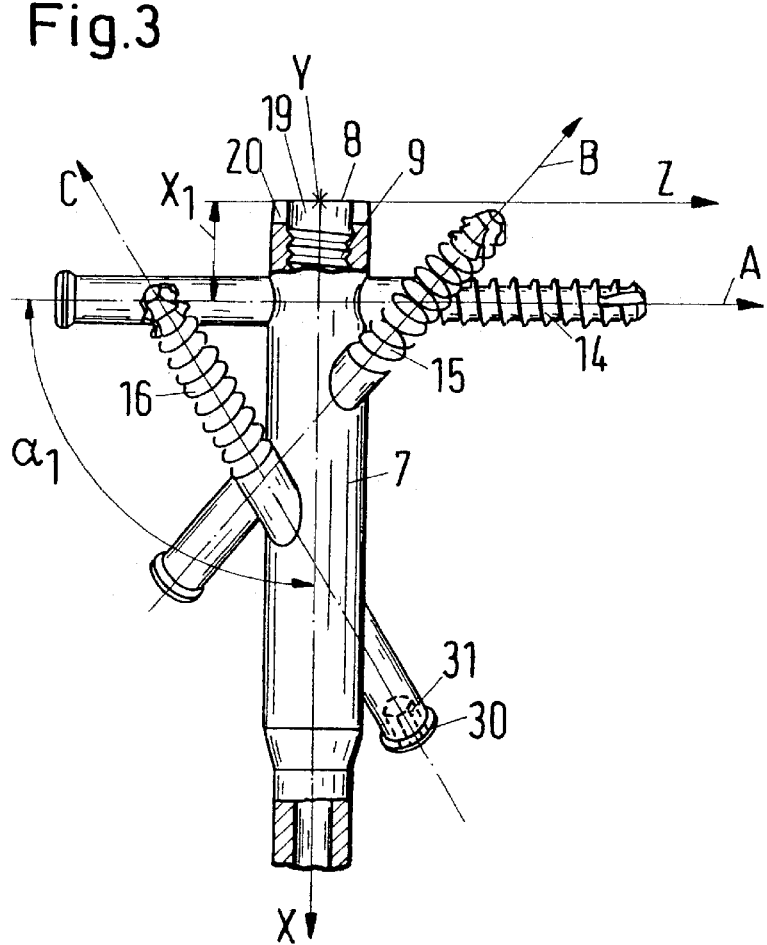
Figure 4:
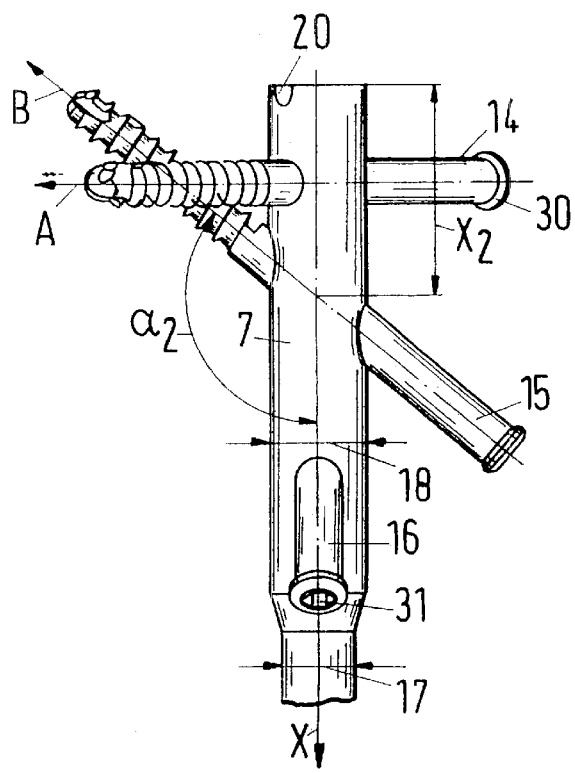
Figure 5:
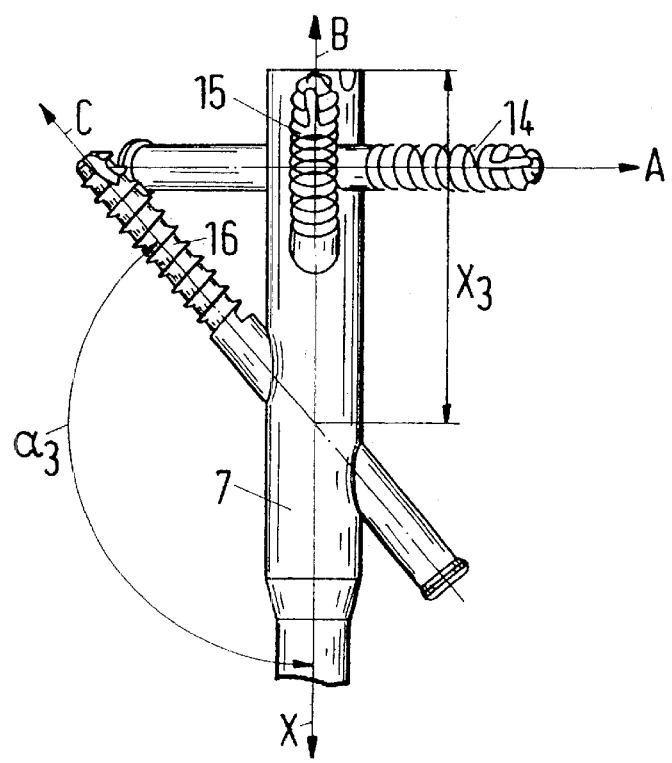
Figure 6:
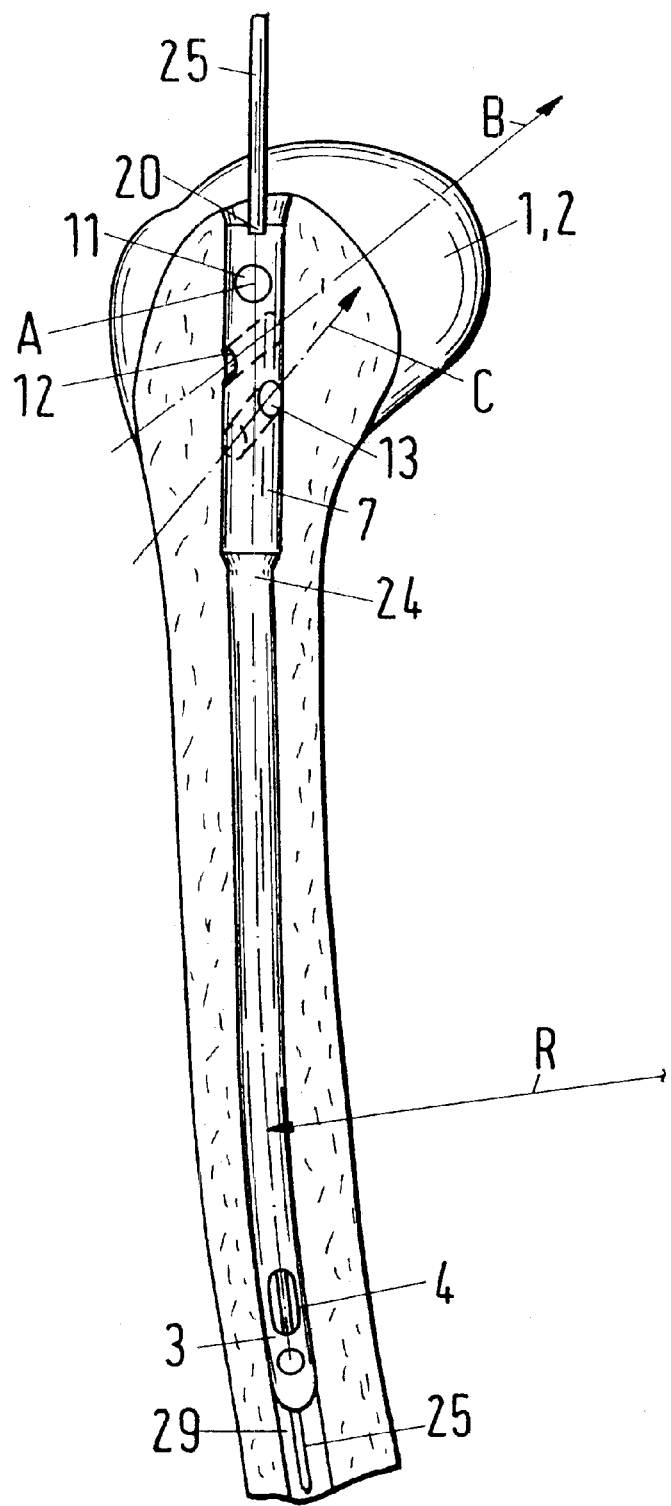
Figure 7:
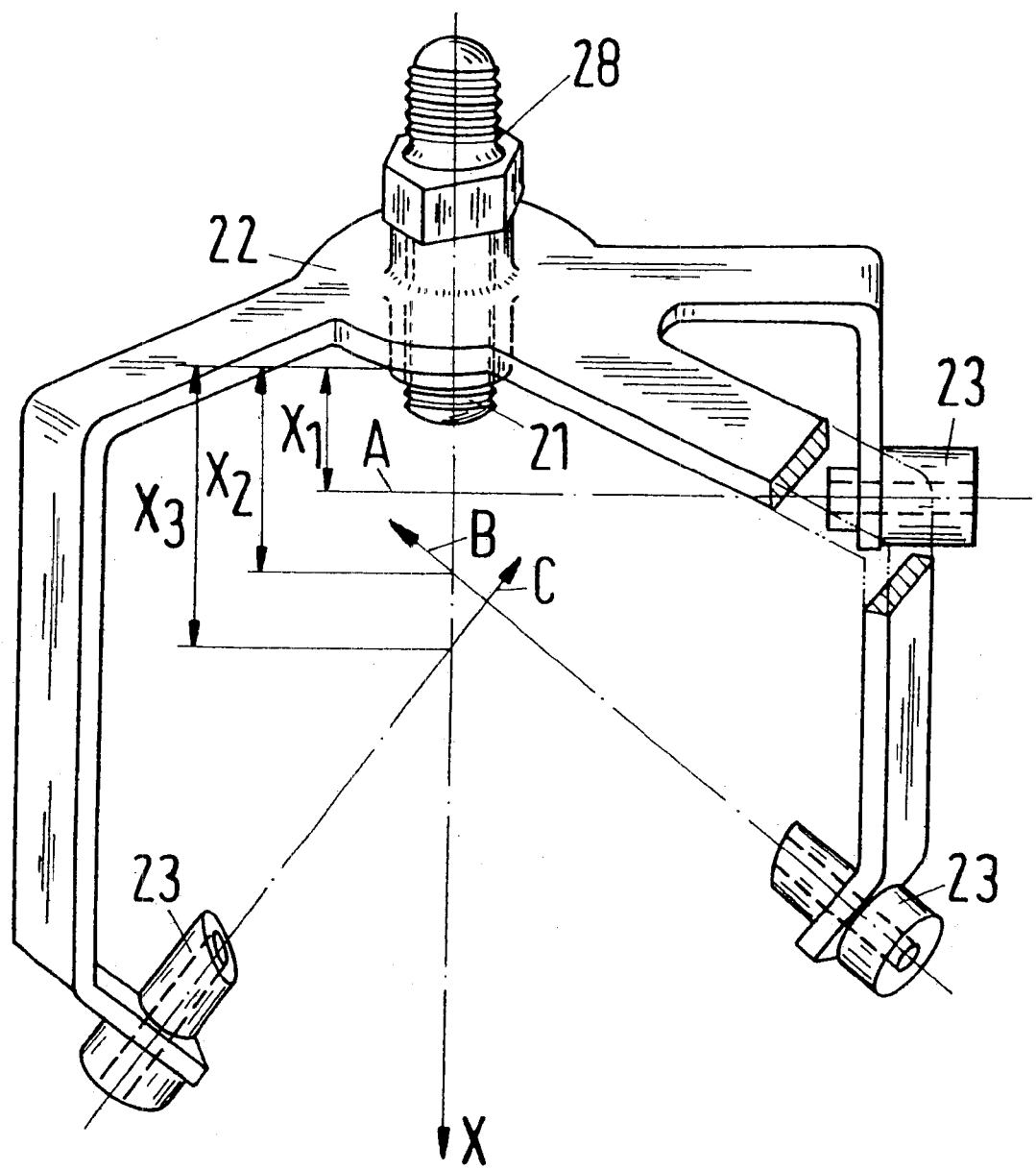

The invention is described by way of embodiments in the following. There are shown:

FIG. 1 in schematic form, the view of a femur marrow nail of the invention with a coordinate system to represent the end piece;

FIG. 2 in schematic form, an enlarged plan view in the direction of the X axis of the end piece of FIG. 1;

FIG. 3 schematically, a side view of the end piece of FIG. 2 in the direction of the Y axis;

FIG. 4 schematically, a side view of the end piece of FIG. 2 perpendicular to a plane which is given by the longitudinal axis X and by the axis B;

FIG. 5 schematically, a side view of the end piece of FIG. 2 perpendicular to a plane which is given by the longitudinal axis X and the axis C;

FIG. 6 schematically, a side view perpendicular to the sagittal plane of a further femur marrow nail which is driven into a femur bone; and FIG. 7 schematically, an enlarged view of a target wire which can be used for the end pieces of FIGS. 1 and 6.

The Figures show a femur marrow nail for insertion between the condylii of a knee joint having an anchoring 4 in the region of the nail tip 3, having a curvature 6 extending in the sagittal plane 5 and having a straight end piece 7 which has fastening bores 12, 13 with axes B, C for its fastening.

At least two fastening bores 12, 13 with axes B and C are applied at a spacing $X_2$, $X_3$ less than 70 millimeters from the end 8 of the end piece 7, whose axes B and C penetrate a plane 10 which includes the end 8 and is perpendicular to the longitudinal axis X at a distance r from the X axis in a region of 10 mm$\leq$r$\leq$116 mm in order to grip hard bone zones with fastening screws in the region of the condylii.

The same reference symbols are used for the same functions in the FIGS.

The marrow nail shown in FIGS. 1 to 5 relates to a right femur and consists of a straight end piece 7 which has a larger diameter 18 than the diameter 17 of the remaining part extending subsequent thereto with a curvature 6 in the sagittal plane 5. The coordinate system in FIG. 1 is arranged such that the longitudinal axis X of the end piece extends in a proximal direction, that the Y axis extending perpendicular to the X axis lies in the sagittal plane 5 with the X axis and extends towards anterior, while the Z axis extends towards medial. The relationships are mirrored accordingly for a marrow nail for the left femur. The marrow nail is hollow and has a continuous opening in the longitudinal direction to guide it at a guide wire during driving in. The end piece 7 is straight and allows the marrow space to be bored from the knee with a mechanical drill. Since the end piece has a larger diameter 18, the curved front part can be inserted without problem. For example, the end piece 7 has a diameter 18 of 18 mm and the curved part a diameter 17 of 10 mm. The curvature 6 of the front shank part corresponds to a curvature radius R between 800 mm up to 1,200 mm. The marrow nail is provided at its nail tip 3 with an anchoring 4 which can consist of transverse bores for bone screws. These can also be designed in the form of an elongate opening to promote the formation of callus at fracture points of the bone with permitted minimum movements in the longitudinal direction. A first transverse bore 11 is applied at a spacing $X_1$ between 10 and 18 mm from the end 8 of the end piece 7 and its axis A extends perpendicular to the X axis and perpendicular to the sagittal plane 5, that is parallel to the Z axis. A plane 10, which includes the end 8 and the axes Y, Z, extends perpendicular to the X axis.

An obliquely applied fastening bore 12 with axis B crosses the longitudinal axis X at a spacing $X_2$ between 20 and 42 mm from the end 8 of the end piece, and an obliquely applied fastening bore 13 with axis C crosses the longitudinal axis X at a spacing $X_3$ between 30 and 70 mm from the end 8. Both fastening bores 12 and 13 are applied such that their axes B and C penetrate the plane 10 at penetration points 26 and 27, with the spacing r of these penetration points from the X axis lying in a range between 10 and 116 mm.

This region is indicated for the penetration points 26 and 27 by a circular ring in the plane 10 in FIG. 1.

For the better understanding of the directions of the axes A, B, C, the associated fastening screws 14, 15, 16 are drawn in FIGS. 2 to 5.

In FIG. 2, there results with respect to the Y axis, respectively to the sagittal plane 5, an angle $\beta_1$ of 90° for the axis A, an angle $\beta_2$ between 35° and 55° for the axis B and an angle $\beta_3$ between 30° and 45° for the axis C at the opposite side to the axis Y.

The side view in the direction of the Y axis in FIG. 3 shows that the axis A extends parallel to the Z axis at the distance $X_1$ and forms an angle $\alpha_1$ of 90° to the X axis. It can further be recognised that the marrow nail is hollow and has at its end 8 a circular guide 19 and a slot 20 as well as an internal thread 9 for the form-locked fastening of a target wire 22 such as is shown in FIG. 7. The fastening screws 16 themselves have a narrow collar 30 and a hex socket 31 for a screwdriver tool at their ends.

FIG. 4 shows, analogue to FIG. 3, that the axis B is arranged at an angle $\alpha_2$ between 110° and 150° to the X axis and crosses the X axis at a spacing $X_2$ between 20 and 42 mm. The larger diameter 18 of the end piece is furthermore provided with a conical transition to the diameter 17 of the front part.

The axis C in FIG. 5 crosses the X axis at a distance $X_3$ between 30 and 70 mm and forms an angle $a_3$ thereto between 30 and 45°.

The marrow nail can have a length between 480 mm and 150 mm. A shorter version is shown in FIG. 6 with respect to FIG. 1. The marrow nail sits—already driven in—in a femur bone in which the fracture boundaries of fragments are not visible. A guide wire 25, along which the marrow nail was driven in, has not yet been removed. The two axes B, C are directed towards posterior into the condylii 1, 2. The marrow nail likewise has a curvature with a curvature radius R in the sagittal plane and, in addition, a kink 24 at the transition to the straight end piece 7. Two transverse bores, one of which is an elongate aperture, are applied at the nail tip 3 for an anchoring 4. The fastening screws are screwed in according to the shown directions of the axes B and C, with the surfaces of the condylii, respectively of condylus fragments, which are supporting towards the outside, remaining unscathed.

A matching centring apparatus with a target wire 22 is shown in FIG. 7, said target wire 22 being able to be fastened in a form-locked manner to a connection screw 28 whose thread 21 engages at the corresponding internal thread 9 (FIG. 3). The centring wire is inwardly centred at a round guide 19, aligned in a planar manner at the end 8 in the Y-Z plane and latches with a shoulder in a form-locked manner at a provided angle position in the slot 20. The connection screw 28 is provided with a hex head in order to screw on the target wire 22 and to screw on a sliding hammer at an upwardly continued thread. The position of the axes A, B, C, which cross the X axis at the spacings $X_1$, $X_2$, $X_3$, is repeated with bore guides 23, in order to bore the bone at the driven-in marrow nail with a guided bore tool at least up to the fastening bores 11, 12, 13 in the end piece 7. The actual wires, which form the connection to the bore guides 23, must project sufficiently far from the X axis that they do not collide with the condylii. On the other hand, the bore guides 23 should be led as closely as possible to the bone to be bored in order to sufficiently guide bore tools applied obliquely to the bone surface. For this reason, it is advantageous first to carry out the bore in the direction of the axis A and to carry out a provisional fixation via this bore, for example, by leaving a bore tool in place, before boring in the axis directions B and C.

What is claimed is:

1. A femur marrow nail for insertion between the condylii (1,2) of a knee joint having an anchoring (4) in the region of the nail tip (3), having a curvature (6) provided in the sagittal plane (5) and having a straight end piece (7) which has fastening bores (12, 13) with axes B, C for its fastening, wherein at least two fastening bores (12, 13) cross the longitudinal axis X of the end piece (7) with axes B and C at a spacing less than 70 millimeters from an end (8) of the end piece (7), and with their axes B and C penetrating a plane (10) which includes the end (8) and is perpendicular to the longitudinal axis X at a distance r from the X axis in a region of 10 mm$\leq$r$\leq$116 mm in order to grip hard bone zones with fastening screws (15, 16) in the region of the condylii (1, 2), wherein, in a projection in the direction of the longitudinal axis X of the end piece (7), the axis C extends in an angle region 30°$\leq\beta_3\leq$45° to the sagittal plane (5).

2. A femur marrow nail for insertion between the condylii (1, 2) of a knee joint having an anchoring (4) in the region of the nail tip (3), having a curvature (6) provided in the sagittal plane (5) and having a straight end piece (7) which has fastening bores (11, 12, 13) with axes A, B, C for its fastening, wherein at least one transverse fastening bore (11) crosses the longitudinal axis of the end piece (7) with an axis A at a spacing $X_1$ from its end (8) and is perpendicular to the sagittal plane (5), wherein at least two fastening bores (12, 13) with their axes B and C penetrating a plane (10) which includes the end (8) and is perpendicular to the longitudinal axis X at a distance r from the X axis in a region of 10 mm$\leq$r$\leq$116 mm in order to grip hard bone zones with fastening screws (15, 16) in the region of the condylii (1,2), wherein the longitudinal axis X is crossed by the axis A at a spacing of $10 \text{ mm} \leq X_1 \leq 18 \text{ mm}$, by the axis B at a spacing of $20 \text{ mm} \leq X_2 \leq 42 \text{ mm}$ and by the axis C at a spacing of $30 \text{ mm} \leq X_3 \leq 70 \text{ mm}$.

3. A femur marrow nail in accordance with claim 2, wherein, in a projection in the direction of the longitudinal axis X of the end piece (7), the axis B extends in an angle region $35° \leq \beta_2 \leq 55°$ to the sagittal plane (5).

4. A femur marrow nail in accordance with claim 2, wherein, in a projection in the direction of the longitudinal axis X of the end piece (7), the axis C extends in an angle region $30° \leq \beta_3 \leq 45°$ to the sagittal plane (5).

5. A femur marrow nail in accordance with claim 2, wherein the axis B forms an angle of $110 \leq \alpha_2 \leq 150°$ relative to the longitudinal axis X.

6. A femur marrow nail in accordance with claim 2, wherein the axis C forms an angle of $125 \leq \alpha_3 \leq 160°$ relative to the longitudinal axis X.

7. A femur marrow nail in accordance with claim 2, wherein the end piece (7) of the femur marrow nail has a greater diameter (18) than that portion of the femur marrow nail having a curvature provided in the sagittal plane.

8. A femur marrow nail in accordance with claim 2, wherein the end piece has a form-locked connection (19, 20, 21) for a target wire (22) with bore guides in the direction of the axes A, B, and C.

9. A femur marrow nail in accordance with claim 2, wherein a transition from the end piece (7) to the further marrow nail is provided with a kink (24) in the sagittal plane of less than 8° of change of direction.

10. A femur marrow nail in accordance with claim 2, wherein the marrow nail is cannulated for a possible guide wire.

11. A femur marrow nail in accordance with claim 2, wherein the marrow nail has an elongate slot outside the end piece (7).

* * * * *